United States Patent [19]

Burckett St. Laurent et al.

[11] Patent Number: 4,578,200

[45] Date of Patent: Mar. 25, 1986

[54] FABRIC SOFTENERS

[75] Inventors: James C. T. R. Burckett St. Laurent, Overijse; Alfred Busch, Grimbergen, both of Belgium

[73] Assignee: The Procter & Gamble Company, Cincinnati, Ohio

[21] Appl. No.: 676,036

[22] Filed: Nov. 29, 1984

[30] Foreign Application Priority Data

Dec. 20, 1983 [GB] United Kingdom ............... 8333815

[51] Int. Cl.$^4$ ........................................ D06M 11/00
[52] U.S. Cl. ................................ 252/8.8; 252/174.23; 252/544; 252/547; 252/DIG. 2
[58] Field of Search .................. 252/DIG. 2, 8.8, 99, 252/174.23, 544, 547

[56] References Cited

U.S. PATENT DOCUMENTS

| | | | |
|---|---|---|---|
| 4,338,204 | 7/1982 | Spadini et al. | 252/544 |
| 4,360,437 | 11/1982 | Wolfes | 252/8.8 |
| 4,381,259 | 4/1983 | Homma et al. | 252/174.23 |
| 4,386,000 | 5/1983 | Turner et al. | 252/8.8 |
| 4,410,588 | 10/1983 | Ling | 252/8.8 |

FOREIGN PATENT DOCUMENTS 1269848  4/1972  United Kingdom .

*Primary Examiner*—Paul Lieberman
*Assistant Examiner*—Willie J. Thompson
*Attorney, Agent, or Firm*—Robert B. Aylor; Richard C. Witte; Thomas H. O'Flaherty

[57] ABSTRACT

Copolymers of maleic anhydride and vinyl ethers are derivatized by $C_{8-20}$ alkyl amines to form alkyl amide-substituted copolymers that exhibit fiber and fabric softening properties. The derivatized copolymers are formulated in a variety of laundry and shampoo compositions.

10 Claims, No Drawings

FABRIC SOFTENERS

TECHNICAL FIELD

The present invention relates to means of treating fibers and fabrics, wherein alkyl amide derivatives of maleic anhydride-vinyl ether copolymers are used to provide softness and anti-static benefits. Detergent compositions containing said amide-derivatized copolymers are disclosed. The compositions herein can be used to soften fabrics, and to soften and "condition" fibres, especially hair.

BACKGROUND

The use of cationic materials to treat hair in a post-shampoo rinse is a well-know cosmetic practice. Likewise, the use of softeners to treat fabrics after a washing operation is a well-known laundering practice. Fabric softeners are, in the main, water-insoluble cationic materials that are incompatible with anionic detersive surfactants used in most fabric washing compositions. For that reason, the softening operation is generally carried out in the laundry rinse bath after the surfactant has been removed from the washing machine. This entails additional work for the user.

Formulators of fabric laundering compositions have long sought means whereby the fabric washing and softening could be done concurrently. The same is true for shampoo formulators, since the problems are rather similar. Laundering methods employing clay softeners, mixtures of clays and various amine materials and the like, are described in the following patents: German Nos. 29/64114.3, 28/57163.3, 24/39541.3, 23/34899.4 and EPO Nos. 80200570.2, 80200877.1 and 80201015.7. The use of mixtures of amines and soaps (salts of fatty acids) as through-the-wash softeners is disclosed in U.K. Pat. No. 1 514 276.

The prior art also describes the use of various cationic materials in sheet form. See U.S. Pat. No. 4, 220, 562.

The present invention employs alkyl amide derivatives of copolymers in laundry or shampoo compositions to provide cleaning and softening concurrently. The amidesubstituted copolymers herein provide improved softening and anti-static benefits, especially when used with clay softeners and/or when the compositions herein are used at moderate laundering temperatures (up to 60° C.). In contrast with monomeric amides taught for use in detergents by the prior art, the amide-/copolymers herein are heat-stable, and can be used in aqueous crutcher mixes to provide spray-dried detergents.

SUMMARY OF THE INVENTION

The present invention encompasses a method for softening fibres or fabrics by contacting same with a $C_{8-20}$ (preferably $C_{10-16}$) alkyl amide derivative of a maleic anhydride-alkyl vinyl ether copolymer in the presence of water. The method can be carried out, for example, by tumbling damp fabrics with said amide-substituted copolymers in a hot air clothes dryer. In another mode, the copolymers can be used in an aqueous rinse bath, for example in a laundry or post-shampoo rinse. In still another mode, the method can be carried-out concurrently with a fibre or fabric cleansing treatment, for example in a detergentcontaining laundry liquor or shampoo, to soften fabrics or hair.

The invention also encompasses detergent compositions (preferably, spray-dried), which may be described succinctly as containing conventional detergent ingredients such as detersive surfactants (including anionics), detergency builders, optical brighteners, detersive enzymes, fabric bleaches, and the like, all at rather conventional levels, as well as clay fabric softeners (preferably, smectite clays), said compositions being characterized in that they contain at least 0.1% (preferably 1.0% to 15%) of the aforesaid alkyl amide-substituted copolymer. The preferred compositions with clay are formulated to contain not more than 3% (preferably not more than 1%–2%) of a nonionic detersive surfactant.

The invention also encompasses an article for use in a laundry bath or rinse bath, or in a laundry dryer, comprising the aforesaid alkyl amide copolymer releasably affixed to a water-insoluble carrier, for example, a sheet of paper or fabric. Such compositions are optionally formulated to contain a bleach activator and such activator-containing compositions are especially useful in laundry baths.

The ingredients and means for preparing the compositions are disclosed more fully hereinafter. All weights and proportions are by weight, unless otherwise specified.

DETAILED DESCRIPTION OF THE INVENTION

As noted hereinafter, the detergent compositions of this invention comprise, in major part, conventional ingredients that are quite familiar to formulators of laundry compositions. One of the major advantages of the alkyl amide derivatives of maleic anhydride-alkyl vinyl ether copolymers used herein is that they are entirely compatible with such conventional detergent ingredients, used at conventional concentrations.

COPOLYMER

The key materials used in the practice of this invention are the $C_{8-20}$ amide derivatives of maleic anhydride-alkyl ether copolymers, of the formula

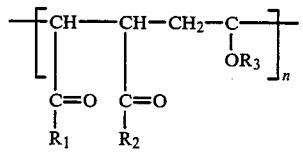

Wherein $R_1$ and $R_2$ represent mono-alkyl (preferred) or dialkyl amino substituents (alkyl being $C_8$–$C_{20}$; preferably $C_{10}$–$C_{16}$); $R_3$ is short-chain alkyl such as methyl, ethyl or propyl, most preferably methyl. It is to be understood that some groups $R_1$ or $R_2$ may be —OH or —O⊖M+(with M being a counterion such as sodium, potassium, alkanolammonium, ammonium, and the like). Stated otherwise, it is not critical that all carboxy units on the maleic anhydride portion of the copolymeric backbone be substituted with amide groups.

The preparation of maleic anhydride-vinyl ether copolymers and their use in detergents is disclosed in U.K. Pat. No. 1 269 848. Various short chain amides and derivatives of such detergent copolymers are mentioend in French Pat. No. 2 029 123. However, the use of the longer chain alkyl ($C_{8-20}$) amide derivatives to soften fibres and fabrics in the manner disclosed herein does not appear to have been contemplated before.

The preparation of the copolymers involves a standard organic synthesis scheme. For example, maleic anhydride is copolymerized with methyl vinyl ether, and the resulting 1:1 random copolymer is then allowed to react with, for example, iso-tridecyl amine, in a standard amidation reaction to form an amide-substituted copolymer that is particularly useful as a fabric softener.

The amide-copolymers useful herein can be either watersoluble, or water-dispersable. Of course, the degree of water solubility and the softener benefits of the copolymers, can be affected by the alkyl chain lengths on substituents $R_1$ and $R_2$, and, importantly, by the degree of polymerization (n), by the ratios of maleic anhydride: vinyl ether, and by the degree to which the maleic anhydride substituents (as acid units) are substituted by the alkyl amide groups.

In general, the molecular weight range of the amide-substituted polymer should be from 2,000 to 200.000, preferably 50.000 to 150.000.

The mole ratio of maleic anhydride: alkyl vinyl ether in the polymer backbone should in general be 5:1 to 1:5 and the integer (n) in the formula is typically 5 to 500, preferably 100 to 350.

The degree of substitution of the maleic acid carboxyl functional groups by $R_1$ or $R_2$ amide groups is 1% to 80%, preferably 10% to 50% of the total available carboxyl groups.

Softener Clay: The above-described amide-substituted copolymers are preferably used in granular detergent compositions, where they are most preferably used in combination with a detergent-compatible clay fabric softener. Such clay softeners are well-known in the detergency patent literature and are in broad commerical use, both in Europe and in the United States. Included among such clay softeners are various heat-treated kaolins and various multi-layer smectites. Preferred clay softeners are smectite softener clays that are described in German patent document No. 2 334 899 and in U.K. Patent No. 1 400 898 which can be referred to for details. Softener clays are used in the preferred compositions at levels of at least 1%, generally 1-20 %, preferably 2-7%.

Detersive Surfactants: The detergent compositions of this invention will contain organic surface-active agents ("surfactants") to provide the usual cleaning benefits associated with the use of such materials.

Detersive surfactants useful herein include well-known synthetic anionic, amphoteric and zwitterionic surfactants. Typical of these are the alkyl benzene sulfonates, alkyl-and alkylether sulfates, paraffin sulfonates, olefin sulfonates, amine oxides, α-sulfonates of fatty acids and of fatty acid esters, and the like, which are well-known from the detergency art. In general, such detersive surfactants contain an alkyl group in the $C_9$–$C_{18}$ range; the anionic detersive surfactants can be used in the form of their sodium, potassium or triethanolammonium salts. U.S. Pat. Nos. 4, 111, 855 and 3, 995, 669 contain detailed listings of such typical detersive surfactants. $C_{11}$–$C_{16}$ alkyl benzene sulfonates, $C_{12}$–$C_{18}$ paraffin-sulfonates and alkyl sulfates are especially preferred in the compositions of the present type.

Also useful herein as the surfactant are the water-soluble soaps, e.g. the common sodium and potassium coconut or tallow soaps well-known in the art.

It is to be understood that the use of typical alkoxylated nonionic surfactants (e.g. the $C_9$–$C_{18}$ alkyl alcohols and alkyl phenols with 5 to 20 ethoxyl groups) should be limited in the practice of this invention to levels of not more than about 3%, preferably not more than 2%, most preferably 0-1%, of the compositions when clay is present as a co-softener, since alkoxylates can interfere with the softening properties of clay. In clay-free compositions, the alkoxylated nonionics can be used at any desired level.

The surfactant component can comprise as little as 1% of the laundry detergent (or shampoo) compositions herein, but generally the compositions will contain 5% to 40%, preferably 6% to 30%, of surfactant. Mixtures of the anionics, such as the alkyl benzene sulfonates, alkyl sulfates and paraffin sulfonates are preferred for through-the-wash cleansing of a broad spectrum of soils and stains from fabric.

Detersive Adjuncts: The compositions herein can contain other ingredients which aid in their cleaning performance. For example, it is highly preferred that through-the-wash detergent compositions contain a detergent builder and/or metal ion sequestrant. Compounds classifiable and well-known in the art as detergent builders include the nitrilotriacetates, polycarboxylates, citrates, water-soluble phosphates such as tri-polyphosphate and sodium ortho- and pyro-phosphates, silicates, and mixtures thereof. Metal ion sequestrants include all of the above, plus materials like ethylenediaminetetraacetate, the amino-polyphosphonates and phosphates (DEQUEST) and a wide variety of other poly-functional organic acids and salts too numerous to mention in detail here. See U.S. Pat. No. 3, 579, 454 for typical examples of the use of such materials in various cleaning compositions. In general, the builder/sequestrant will comprise about 0.5% to 45% of the composition. The 1–10 micron size zeolite (e.g. zeolite A) builders disclosed in German Pat. No. 2 422 655 are especially preferred for use in low-phosphate compositions which contain the softeners described herein.

The laundry compositions herein also preferably contain enzymes to enhance their through-the-wash cleaning performance on a variety of soils and stains. Amylase and protease enzymes suitable for use in detergents are well-known in the art and in commercially available liquid and granular detergents. Commercial detersive enzymes (preferably a mixture of amylase and protease) are typically used at levels of 0.001% to 2%, and higher, in the present compositions.

Moreover, the compositions herein can contain, in addition to ingredients already mentioned, various other optional ingredients typically used in commercial products to provide aesthetic or additional product performance benefits. Typical ingredients include pH regulants, perfumes, dyes, bleaches, optical brighteners, soil suspending agents, hydrotropes and gel-control agents, freeze-thaw stabilizers, bactericides preservatives, suds control agents, bleach activators and the like.

In a through-the-wash laundry mode, the compositions are typically used at a concentration of at least 500 ppm, preferably 0.10% to 2.5%, in an aqueous laundry bath at pH 7-11 to launder fabrics. The laundering can be carried out over the range from 5° C. to the boil, with excellent results.

In an alternate mode, the amide-substituted copolymers herein may be releasably adsorbed or releasably coated onto a non-particulate substrate such as a nonwoven or paper sheet or flexible sponge mat, or the like. Such sheet-form objects may be added to the laundry or rinse bath, or to the laundry dryer, where the amide-substituted copolymers is released to provide fabric softening. In an alternate, and highly preferred, mode the amide-substituted copolymer is used in sheet form in combination with a bleach activator (such as tetraacetyl ethylene diamine or a straight-or branched-chain $C_6$–$C_{10}$ oxygenzene sulfonate) as a combined perborate-activator and softener in a laundry liquor. See, for example U.S. Pat. No. 4, 220, 562.

Such sheet-form products will generally emply 1-20 grams of the amide-substituted copolymer and 1-20 grams of the bleach activator.

In still another mode, the amide-copolymer can be formulated as a liquid fabric softener and used in a post-laundry rinse bath. Such softeners can comprise, for example, a simple dispersion or solution of the copolymer in water or water-alcohol. Typical concentrations of the copolymer in such compositions are 1-25%.

It is to be understood that the compositions and processes of this invention are formulated carried out in a manner that will, typically, deposit at least a few milligrams (generally, at least 1-1000 mg) of the amide-substituted copolymer per square meter on the fabric or fibre being treated, as will be seen in the following examples.

INDUSTRIAL APPLICATION

The following examples are typical of the preferred composition of this invention, but are not intended to limit the scope of the invention.

EXAMPLE I

An aqueous crutcher mix comprising the following ingredients is prepared and spray-dried in standard fashion (percentages listed relate to percent ingredients in the complete formulation after spray--drying).

| Ingredients | Percent |
| --- | --- |
| $C_{11-12}$ alkyl benzene sulfonate | 6.2 |
| Tallow alcohol ethoxylate (EO11) | 1.0 |
| Sodium perborate | 20.0 |
| Sodium tripolyphosphate | 24.0 |
| Sodium sulfate | 22.0 |
| Sodium silicate | 8.0 |
| Smectite clay* | 2.4 |
| Ditallow methyl amine | 3.8 |
| Alkyl Amide copolymer** | 1.6 |
| Carboxymethyl cellulose | 0.4 |
| Enzymes | 0.5 |
| Optical brightener | 0.23 |
| Sulphonated zinc phthalocyanine*** | 25 ppm |
| EDTA | 0.2 |
| Perfume/copper salts/minors/brightener | 0.5 |
| Suds suppressor | 2.7 |
| Moisture | to 100 |

*Natural smectite; $CaCO_3$ ion exchange capacity above 50 meq/100 g clay
**Isotridecyl amine derivative of maleic anhydride-methyl vinyl ether (MVE) copolymer; range of (n) 100 to 350; molar ratio maleic: MVE 1:1; avg. degree of substitution of maleic by isotridecyl amine 1:0.4.
***U.S. Pat. No. 3 927 967

The composition of Example I is free-flowing and provides exellent cleaning and through-the-wash fabric softening when used at laundry concentration of 0.1%, and above.

The composition of Example I may be modified by adding 1.0% tetraacetyl ethylenediamine (TAED) as a perborate bleach activator.

EXAMPLE II

A nil-P spray-dried detergent formulation is as follows:

| Ingredient | Percent |
| --- | --- |
| Zeolite A (1-10 micron) | 26.0 |

-continued

| Ingredient | Percent |
| --- | --- |
| Sodium nitrilotriacetate | 5.0 |
| Smectite clay* | 3.0 |
| Alkyl Amide Copolymer** | 2.5 |
| $C_{11-12}$ alkyl benzene sulfonate (Na) | 6.5 |
| Tallow ethoxylate (EO 9-11) | 0.5 |
| Sodium perborate.$4H_2O$ | 20.0 |
| Sodium silicate | 8.0 |
| CMC | 1.0 |
| Sodium sulfate | 20.0 |
| Enzymes (1:1 amylase/protease) | 1.5 |
| Optical brightener | 0.5 |
| TAED | 1.2 |
| Water, minors | to 100 |

*As Gelwhite GP TM; $CaCO_3$ ion exchange capacity > 70 Meq/100 g.
**As in Example I, with diethylhexyl amine replacing isotridecyl.

The composition of Example II is prepared by spray-drying an aqueous crutcher mix. In use, the composition gives excellent cleaning and through-the-wash fabric softening performance.

EXAMPLE III

A laundry additive product is prepared by warming 6.5 g of a copolymer of maleic anhydride: ethyl vinyl ether derivatized with diethylhexyl amine (avg. n 175; mole ratio maleic: EVE 1:1; avg. degree of substitution of maleic by diethylhexyl amine 1:0.4) and spreading the melt onto an ordinary disposable paper hand-towel (20×20 cm). 4 grams of TAED powder (1–10 microns) are sprinkled onto, and pressed into, the melt before it has the chance to solidify.

The article of Example III is added to a laundry liquor containing a commercial perborate/clay detergent composition (DASH-3; Trademark) to enhance through-the-wash softening and bleaching performance.

EXAMPLE IV

The article of Example III is modified by deleting the TAED and replacing the diethylhexyl amide-copolymer with 3.5 g. of the alkyl amide copolymer of Examples I and II. The resulting article is tumbled with damp fabrics in a standard hot air clothes dryer, whereby the alkyl amide copolymer is transferred to the fabrics to impart softness.

EXAMPLE V

A shampoo composition with hair-conditioning properties is as follows:

| Ingredient | Percent |
| --- | --- |
| $C_{10-14}$ Alkyl Sulfate | 9.0 |
| Tallow alkyl benzene sulfonate | 2.0 |
| Coconut Soap | 4.0 |
| Glycerine | 3.0 |
| Alkyl Amide Copolymer* | 6.0 |
| Triethanolamine | to pH 7.0 |
| Perfume | 0.25 |
| Water | to 100 |

*The copolymer of Example I.

We claim:
1. A method of softening fibres or fabrics which comprises contacting said fibres or fabrics with a $C_{8-20}$ alkyl amide derivative of a maleic anhydride-alkyl vinyl ether copolymer in the presence of water.
2. A method according to claim 1 which is carried-out in an aqueous laundry liquor or shampoo.

3. A method according to claim 1 which is carried-out by tumbling damp fabrics with said alkyl amide-copolymer in a hot air clothes dryer.

4. A laundry detergent composition comprising conventional detersive ingredients, characterized in that it contains at least 0.1% of a $C_{8-20}$ alkyl amide derivative of a maleic anhydride-alkyl vinyl ether copolymer.

5. A composition according to claim 4 which contains from 1% to 15% of the alkyl amide copolymer.

6. A composition according to claim 5 which contains at least 1% of a smectite clay softener.

7. A composition according to claim 6 which contains not more than 3% of an alkoxylated nonionic detersive surfactant.

8. A composition according to claim 4 which contains a detergency builder selected from phosphate, nitrilotriacetate, polycarboxylate, citrate and zeolite builders, or mixtures thereof.

9. An article for use in a laundry or rinse bath, or in a laundry dryer, comprising a non-particulate substrate, preferably a flexible sheet, having releasably affixed thereto a $C_{8-20}$ alkyl amide derivative of a maleic anhydride-alkyl vinyl ether copolymer.

10. An article according to claim 9 which additionally has affixed thereto a bleach activator.

* * * * *